United States Patent
Takemura et al.

(10) Patent No.: US 9,914,799 B2
(45) Date of Patent: Mar. 13, 2018

(54) COMPOSITION FOR OPTICAL MATERIAL AND METHOD FOR PRODUCING SAME, AND OPTICAL MATERIAL PRODUCED FROM COMPOSITION FOR OPTICAL MATERIAL

(71) Applicant: MITSUBISHI GAS CHEMICAL COMPANY, INC., Tokyo (JP)

(72) Inventors: Kouhei Takemura, Osaka (JP); Tetsuya Konishi, Osaka (JP); Takashi Aoki, Osaka (JP); Hiroshi Horikoshi, Tokyo (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 0 days.

(21) Appl. No.: 15/119,854

(22) PCT Filed: Apr. 10, 2015

(86) PCT No.: PCT/JP2015/061206
§ 371 (c)(1),
(2) Date: Aug. 18, 2016

(87) PCT Pub. No.: WO2015/159811
PCT Pub. Date: Oct. 22, 2015

(65) Prior Publication Data
US 2017/0051095 A1    Feb. 23, 2017

(30) Foreign Application Priority Data

Apr. 14, 2014 (JP) ................. 2014-082880
Apr. 14, 2014 (JP) ................. 2014-082881

(51) Int. Cl.
C08G 18/38   (2006.01)
C07D 331/02  (2006.01)
G02B 1/04    (2006.01)
C08G 18/75   (2006.01)

(52) U.S. Cl.
CPC ....... *C08G 18/3874* (2013.01); *C07D 331/02* (2013.01); *C08G 18/3876* (2013.01); *C08G 18/755* (2013.01); *G02B 1/041* (2013.01)

(58) Field of Classification Search
CPC .. G02B 1/041; C08G 18/3874; C08G 18/755; C08G 18/3876; C07D 331/02
See application file for complete search history.

(56) References Cited

U.S. PATENT DOCUMENTS 6,472,495 B1  10/2002  Yoshimura et al.
7,309,794 B1* 12/2007  Amagai ............ C07D 331/02
                                              549/90
2003/0149231 A1* 8/2003  Amagai ............ C07D 331/02
                                              528/377
2012/0123081 A1* 5/2012  Okada ................. G02B 1/04
                                              528/84
2012/0309932 A1  12/2012  Takemura et al.
2015/0028270 A1   1/2015  Tanaka et al.
2015/0203633 A1   7/2015  Takemura et al.

FOREIGN PATENT DOCUMENTS

| EP | 1 518 873 | 3/2005 |
|---|---|---|
| JP | 9-110979 | 4/1997 |
| JP | 11-256038 A * | 9/1999 |
| JP | 11-352302 | 12/1999 |
| JP | 2001-2783 | 1/2001 |
| JP | 2001-131257 | 5/2001 |
| JP | 2001-330701 | 11/2001 |
| JP | 2004-137481 | 5/2004 |
| JP | 2005-220162 | 8/2005 |
| JP | 2007-90574 | 4/2007 |
| JP | 2011-219389 A * | 11/2011 |
| JP | 2011-231305 | 11/2011 |
| JP | 2011-251940 A * | 12/2011 |
| JP | 2012-167199 | 9/2012 |
| JP | 2013-142073 | 7/2013 |
| JP | 2013-142073 A * | 7/2013 |
| WO | 2011/105320 | 9/2011 |
| WO | 2013/133144 | 9/2013 |

OTHER PUBLICATIONS

International Search Report issued in Patent Application No. PCT/JP2015/061206, dated Jun. 9, 2015.
Extended European Search Report for EP 15 77 9966 dated Nov. 21, 2017 in English.

* cited by examiner

*Primary Examiner* — Rabon Sergent
(74) *Attorney, Agent, or Firm* — Greenblum & Bernstein, P.L.C.

(57) ABSTRACT

According to the present invention, a composition for an optical material can be provided, which is characterized by containing an episulfide compound having a value of turbidity in acetone of 3.0 ppm or less. According to a preferred embodiment of the present invention, a composition for an optical material can be provided, which comprises: (a) a compound (an episulfide compound) which has a structure represented by formula (1) and has a value of turbidity in acetone of 3.0 ppm or less; (b) a polyisocyanate compound; and (c) a polythiol compound.

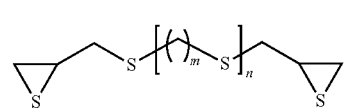

(1)

(In the formula, m represents an integer of 0 to 4; and n represents an integer of 0 or 1.)

19 Claims, No Drawings

COMPOSITION FOR OPTICAL MATERIAL AND METHOD FOR PRODUCING SAME, AND OPTICAL MATERIAL PRODUCED FROM COMPOSITION FOR OPTICAL MATERIAL

TECHNICAL FIELD

The present invention relates to a composition for optical materials, etc., and particularly relates to a composition for optical materials suitable for optical materials for a plastic lens, a prism, an optical fiber, an information recording substrate, a filter or the like, in particular for a plastic lens, and the like.

BACKGROUND ART

Plastic materials are lightweight, highly tough and easy to be dyed, and therefore are widely used recently for various types of optical materials, particularly eyeglass lenses. Optical materials, particularly eyeglass lenses, are specifically required to have, as physical properties, low specific gravity, high transparency and low yellowness, high heat resistance, high strength and the like, and as optical properties, high refractive index and high Abbe number. A high refractive index allows a lens to be thinner, and a high Abbe number reduces the chromatic aberration of a lens. However, as the refractive index is increased, the Abbe number is decreased. Therefore, it has been studied to improve both of the refractive index and the Abbe number. Among methods which have been proposed, the most representative method is a method using an episulfide compound as described in Patent Document 1.

Moreover, it has been studied to achieve a high refractive index, and compositions consisting of sulfur, an episulfide compound and thiol described in Patent Documents 2 and 3 have been proposed.

Furthermore, optical materials obtained by introducing thiourethane in a polyepisulfide compound in order to improve the strength have been reported (Patent Documents 4 and 5).

However, when thiourethane is introduced, it causes reduction in heat resistance, generation of odor at the time of cutting work and occurrence of uneven polymerization called striae, and for this reason, techniques in which a composition ratio is limited or a viscosity is limited have been reported (Patent Documents 6-8).

However, white turbidity may occur in these compositions containing an episulfide compound when polymerized and cured. Since compositions are used for optical materials, when white turbidity occurs after curing, all becomes defective products, resulting in heavy losses. Accordingly, a technique which makes it possible to predict whether or not white turbidity will occur after curing and to determine quality at a stage before curing has been desired.

PRIOR ART DOCUMENTS

Patent Documents

Patent Document 1: Japanese Laid-Open Patent Publication No. H09-110979
Patent Document 2: Japanese Laid-Open Patent Publication No. 2001-2783
Patent Document 3: Japanese Laid-Open Patent Publication No. 2004-137481
Patent Document 4: Japanese Laid-Open Patent Publication No. H11-352302
Patent Document 5: Japanese Laid-Open Patent Publication No. 2001-131257
Patent Document 6: Japanese Laid-Open Patent Publication No. 2001-330701
Patent Document 7: Japanese Laid-Open Patent Publication No. 2005-220162
Patent Document 8: Japanese Laid-Open Patent Publication No. 2007-090574

SUMMARY OF THE INVENTION

Problems to be Solved by the Invention

The problem to be solved by the present invention is to provide a composition for optical materials comprising an episulfide compound, etc., wherein it is possible to predict and judge the possibility of occurrence of white turbidity after curing and judge whether it is good or bad prior to polymerization and curing.

Means for Solving the Problems

In consideration of such circumstances, the present inventors diligently made researches and solved the problem with a composition for optical materials comprising an episulfide compound, wherein a value of turbidity in a solution measured when the episulfide compound is dissolved in acetone (a value of turbidity in acetone) is 3.0 ppm or less, etc., and thus arrived at the present invention.

Specifically, the present invention is as follows:

<1> A composition for optical materials, which comprises an episulfide compound having a value of turbidity in acetone of 3.0 ppm or less.

<2> The composition for optical materials according to item <1>, further comprising a sulfur.

<3> The composition for optical materials according to item <2>, wherein the episulfide compound is preliminarily polymerized with the sulfur.

<4> The composition for optical materials according to item <2> or <3>, wherein 10% or more of the sulfur is preliminarily polymerized with the episulfide compound.

<5> The composition for optical materials according to any one of items <2> to <4>, further comprising a polythiol compound.

<6> The composition for optical materials according to any one of items <1> to <5>, which is subjected to the deaeration treatment.

<7> The composition for optical materials according to item <1>, wherein the episulfide compound is a compound (a) having the structure represented by formula (1) below:

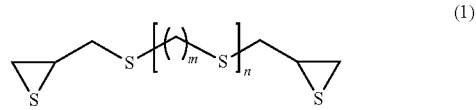

(1)

wherein m represents an integer from 0 to 4, and n represents an integer of 0 or 1.

<8> The composition for optical materials according to item <7>, further comprising a polyisocyanate compound (b) and a polythiol compound (c).

<9> The composition for optical materials according to item <8>, wherein the compound (b) is at least one compound selected from the group consisting of isophorone diisocyanate, tolylene diisocyanate, diphenylmethane diisocyanate, hexamethylene diisocyanate, m-xylylene diisocyanate, p-xylylene diisocyanate, m-tetramethyl xylylene diisocyanate, p-tetramethyl xylylene diisocyanate, 1,3-bis(isocyanatemethyl)cyclohexane, 1,4-bis(isocyanatemethyl)cyclohexane, bis(isocyanatemethyl)norbornene and 2,5-diisocyanatemethyl-1,4-dithiane, and the compound (c) is at least one compound selected from the group consisting of bis(2-mercaptoethyl)sulfide, 2,5-dimercaptomethyl-1,4-dithiane, 1,3-bis(mercaptomethyl)benzene, 1,4-bis(mercaptomethyl)benzene, 4-mercaptomethyl-1,8-dimercapto-3,6-dithiaoctane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, 1,1,3,3-tetrakis(mercaptomethylthio)propane, pentaerythritol tetrakis-mercaptopropionate, pentaerythritol tetrakis-thioglycolate, trimethylolpropane tris(thioglycolate) and trimethylolpropane tris(mercapto propionate).

<10> The composition for optical materials according to item <8> or <9>, wherein, when the total amount of the compound (a), the compound (b) and the compound (c) is 100 wt %, the compound (a) is in an amount of 50 to 95 wt %; the compound (b) is in an amount of 1 to 25 wt %; and the compound (c) is in an amount of 1 to 25 wt %, and wherein the ratio of the SH groups in the compound (c) to the NCO groups in the compound (b), i.e., [the number of the SH groups in the compound (c)/the number of the NCO groups in the compound (b)] (SH group/NCO group) is 1.0 to 2.5.

<11> A method for producing an optical material, which comprises polymerizing and curing the composition for optical materials according to any one of items <1> to <10>.

<12> A method for producing an optical material, which comprises adding an onium salt, as a polymerization catalyst, to the composition for optical materials according to any one of items <8> to <10> in an amount of 0.0001 to 10 wt % relative to the total amount of the compounds (a) to (c) and polymerizing and curing the mixture.

<13> The method for producing an optical material according to item <11> or <12>, which comprises polymerizing and curing the composition for optical materials and then annealing it.

<14> An optical material obtained by the method for producing an optical material according to any one of items <11> to <13>.

<15> An optical lens comprising the optical material according to item <14>.

<16> A method for producing a raw material for optical materials from a product of an episulfide compound, wherein a product of an episulfide compound having a value of turbidity in acetone of 3.0 ppm or less is selected to be made into the raw material for optical materials.

<17> The method for producing a raw material for optical materials according to item <16>, wherein the episulfide compound is a compound (a) having the structure represented by formula (1) below:

(1)

wherein m represents an integer from 0 to 4, and n represents an integer of 0 or 1.

Advantageous Effect of the Invention

According to the present invention, it is possible to provide a composition for optical materials comprising an episulfide compound, etc., wherein it is possible to predict the possibility of occurrence of white turbidity after polymerization and curing and judge whether it is good or bad prior to polymerization and curing, which was difficult to be carried out by conventional techniques.

EMBODIMENTS FOR CARRYING OUT THE INVENTION

Hereinafter, the first embodiment of the present invention will be described.

The first embodiment of the present invention is a composition for optical materials, which comprises an episulfide compound having a value of turbidity in acetone of 3.0 ppm or less.

The episulfide compound in the first embodiment (and the second embodiment described later) of the present invention does not necessarily mean a pure product, and includes a product of an episulfide compound produced according to a publicly-known method. Specifically, the episulfide compound in the present invention includes a product of an episulfide compound containing a small amount of impurities.

The episulfide compound to be used in the first embodiment of the present invention includes all episulfide compounds, and specific examples thereof are classified into a compound having a chain aliphatic skeleton, a compound having an aliphatic cyclic skeleton and a compound having an aromatic skeleton and listed below.

Examples of the compound having a chain aliphatic skeleton include a compound represented by the following formula (1):

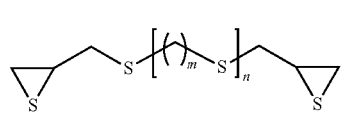
(1)

wherein m represents an integer from 0 to 4, and n represents an integer of 0 or 1.

Examples of the compound having an aliphatic cyclic skeleton include a compound represented by the following formula (2) or (3):

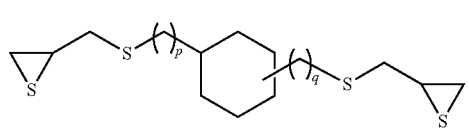
(2)

wherein p and q each independently represent an integer from 0 to 4;

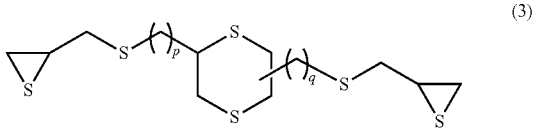

(3)

wherein p and q each independently represent an integer from 0 to 4.

Examples of the compound having an aromatic skeleton include a compound represented by the following formula (4):

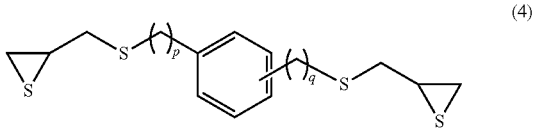

(4)

wherein p and q each independently represent an integer from 0 to 4.

Among them, the compound represented by formula (1) above having a chain aliphatic skeleton is preferred, and specific examples thereof include bis(β-epithiopropyl)sulfide, bis(β-epithiopropyl)disulfide, bis(β-epithiopropyl)trisulfide, bis(β-epithiopropylthio)methane, 1,2-bis(β-epithiopropylthio)ethane, 1,3-bis(β-epithiopropylthio)propane, 1,4-bis(β-epithiopropylthio)butane and bis(β-epithiopropylthioethyl)sulfide. Particularly preferred are bis(β-epithiopropyl)sulfide (n=0 in formula (1) above) and bis(β-epithiopropyl)disulfide (m=0 and n=0 in formula (1) above), and most preferred is bis(β-epithiopropyl)sulfide (n=0 in formula (1) above).

Examples of the episulfide compound having an aliphatic cyclic skeleton include 1,3- and 1,4-bis(β-epithiopropylthio)cyclohexane (p=0 and q=0 in formula (2) above), 1,3- and 1,4-bis(β-epithiopropylthiomethyl)cyclohexane (p=1 and q=1 in formula (2) above), bis[4-(β-epithiopropylthio)cyclohexyl]methane, 2,2-bis[4-(β-epithiopropylthio)cyclohexyl]propane, bis[4-(β-epithiopropylthio)cyclohexyl]sulfide, 2,5-bis(β-epithiopropylthio)-1,4-dithiane (p=0 and q=0 in formula (3) above) and 2,5-bis(β-epithiopropylthioethyl)-1,4-dithiane.

Examples of the episulfide compound having an aromatic skeleton include 1,3- and 1,4-bis(β-epithiopropylthio)benzene (p=0 and q=0 in formula (4) above), 1,3- and 1,4-bis(β-epithioproplythiomethyl)benzene (p=1 and q=1 in formula (4) above), bis[4-(β-epithiopropylthio)phenyl]methane, 2,2-bis[4-(β-epithiopropylthio)phenyl]propane, bis[4-(β-epithiopropylthio)phenyl]sulfide, bis[4-(β-epithiopropylthio)phenyl]sulfine and 4,4-bis(β-epithiopropylthio)biphenyl.

In the first embodiment (and the second embodiment described later) of the present invention, an episulfide compound having a value of turbidity in acetone of 3.0 ppm or less is used. The value of turbidity in acetone in the first embodiment (and the second embodiment described later) of the present invention is a value of turbidity obtained according to the below-described measurement method.

The turbidity in a solution measured when the episulfide compound is dissolved in acetone (turbidity in acetone) is measured according to JIS K0101 using an integrating-sphere turbidimeter with Kaolin standard solution as a standard.

Specifically, 40 g of acetone is added to 10 g of the episulfide compound, the mixture is sufficiently stirred and then allowed to stand for 10 minutes, and the turbidity of this solution is measured.

Acetone: special grade acetone, 99.5% or more (manufactured by Kanto Chemical Co., Inc.)

Turbidimeter: T-2600DA manufactured by Tokyo Denshoku Co., Ltd.

The measurement is carried out, and an episulfide compound having a value of turbidity in acetone of 3.0 ppm or less is used. The value of turbidity in acetone is preferably 1.5 ppm or less, more preferably 0.8 ppm or less, and particularly preferably 0.6 ppm or less.

When the value of turbidity in acetone exceeds 3.0 ppm, white turbidity occurs in an optical material such as a lens after polymerization and curing, and such an optical material with white turbidity is unusable. Accordingly, by measuring the value of turbidity, it is possible to predict and judge the possibility of occurrence of white turbidity and judge whether the episulfide compound is good or bad without polymerization and curing.

In the practical operation, firstly the value of turbidity in acetone is measured, and when the value of turbidity in acetone is within the above-described range, white turbidity does not occur, and accordingly it is judged that the episulfide compound can be used.

Thus, in the first embodiment (and the second embodiment described later) of the present invention, an episulfide compound having a value of turbidity in acetone of 3.0 ppm or less is selected to be made into a raw material for optical materials. In this regard, the method for selecting an episulfide compound is not particularly limited as long as an episulfide compound having a value of turbidity in acetone of 3.0 ppm or less can be selected thereby. For example, as described above, an episulfide compound may be selected by directly measuring the value of turbidity in acetone. Alternatively, an episulfide compound having a value of turbidity in acetone of 3.0 ppm or less may be selected by reference to a value of turbidity of an acetone solution of an episulfide compound having a certain concentration. That is, any method may be employed as long as an episulfide compound having a value of turbidity in acetone of 3.0 ppm or less can be substantially selected thereby.

In the first embodiment of the present invention, sulfur may be added to the composition for optical materials. When sulfur is used, preferably, the sulfur is preliminarily polymerized with the episulfide compound in advance. Conditions for this preliminary polymerization reaction are preferably −10° C. to 120° C. and 0.1 to 240 hours, more preferably 0 to 100° C. and 0.1 to 120 hours, and particularly preferably 20 to 80° C. and 0.1 to 60 hours. It is effective to use a catalyst for promoting the preliminary reaction, and preferred examples thereof include 2-mercapto-1-methylimidazole, triphenylphosphine, 3,5-dimethylpyrazole, N-cyclohexyl-2-benzothiazolylsulfinamide, dipentamethylene thiuramtetrasulfide, tetrabutyl thiuram disulfide, tetraethyl thiuram disulfide, 1,2,3-triphenylguanidine, 1,3-diphenylguanidine, 1,1,3,3-tetramethyleneguanidine, aminoguanidineurea, trimethylthiourea, tetraethylthiourea, dimethylethylthiourea, zinc dibutyldithiocarbamate, zinc dibenzyldithiocarbamate, zinc diethyldithiocarbamate, zinc dimethyldithiocarbamate and pipecorium pipecolyldithiocarbamate. Moreover, it is preferred that 10% or more of the sulfur is consumed by this preliminary polymerization reaction (when the amount of the sulfur before the reaction is regarded as 100%), and it is more preferred that 20% or more of the sulfur is consumed thereby. The preliminary reaction may be performed in any atmosphere, for example, under inert gas such as air, nitrogen or the like, in a sealed state under normal pressure or raised or reduced pressure, or the like. In order to detect how much the preliminary reaction has proceeded, liquid chromatography or a refractometer can be used.

The amount of the sulfur to be used in a preferred embodiment of the present invention is usually 0.1 to 40 parts by weight, preferably 0.5 to 30 parts by weight, and particularly preferably 5 to 25 parts by weight, when the amount of the episulfide compound is 100 parts by weight.

In the first embodiment of the present invention, a polythiol compound may be added to the composition for optical materials. The polythiol compound to be used in the first embodiment of the present invention includes all polythiol compounds, and specific examples thereof include methanedithiol, 1,2-dimercaptoethane, 2,2-dimercaptopropane, 1,3-dimercaptopropane, 1,2,3-trimercaptopropane, 1,4-dimercaptobutane, 1,6-dimercaptohexane, bis(2-mercaptoethyl)sulfide, 1,2-bis(2-mercaptoethylthio)ethane, 1,5-dimercapto-3-oxapentane, 1,8-dimercapto-3,6-dioxaoctane, 2,2-dimethylpropane-1,3-dithiol, 3,4-dimethoxybutane-1,2-dithiol, 2-mercaptomethyl-1,3-dimercaptopropane, 2-mercaptomethyl-1,4-dimercaptopropane, 2-(2-mercaptoethylthio)-1,3-dimercaptopropane, 1,2-bis(2-mercaptoethylthio)-3-mercaptopropane, 1,1,1-tris(mercaptomethyl)propane, tetrakis(mercaptomethyl)methane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, 1,1,3,3-tetrakis(mercaptomethylthio)propane, ethyleneglycolbis(2-mercaptoacetate), ethyleneglycolbis(3-mercaptopropionate), 1,4-butanediolbis(2-mercapto acetate), 1,4-butanediolbis(3-mercaptopropionate), trimethylolpropanetris(2-mercaptoacetate), trimethylolpropanetris(3-mercaptopropionate), pentaerythritoltetrakis(2-mercaptoacetate), pentaerythritoltetrakis(3-mercaptopropionate), 1,1-dimercaptocyclohexane, 1,2-dimercaptocyclohexane, 1,3-dimercaptocyclohexane, 1,4-dimercaptocyclohexane, 1,3-bis(mercaptomethyl)cyclohexane, 1,4-bis(mercaptomethyl)cyclohexane, 2,5-bis(mercaptomethyl)-1,4-dithiane, 2,5-bis(mercaptoethyl)-1,4-dithiane, 1,2-bis(mercaptomethyl)benzene, 1,3-bis(mercaptomethyl)benzene, 1,4-bis(mercaptomethyl)benzene, bis(4-mercaptophenyl)sulfide, bis(4-mercaptophenyl)ether, 2,2-bis(4-mercaptophenyl)propane, bis(4-mercaptomethylphenyl)sulfide, bis(4-mercaptomethylphenyl)ether and 2,2-bis(4-mercaptomethylphenyl)propane.

Among the above-described compounds, specific examples of preferred compounds include bis(2-mercaptoethyl)sulfide, pentaerythritoltetrakis(2-mercaptoacetate), pentaerythritoltetrakis(3-mercaptopropionate), 2,5-bis(mercaptomethyl)-1,4-dithiane, 1,2-bis(2-mercaptoethylthio)-3-mercaptopropane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, 1,1,3,3-tetrakis(mercaptomethylthio)propane, 1,3-bis(mercaptomethyl)benzene and 1,4-bis(mercaptomethyl)benzene. Specific examples of more preferred compounds include bis(2-mercaptoethyl)sulfide and 1,3-bis(mercaptomethyl)benzene, and bis(2-mercaptoethyl)sulfide is most preferred.

When the total amount of the episulfide compound and the sulfur is 100 parts by weight, the amount of the polythiol compound to be used in the first embodiment of the present invention is usually 1 to 30 parts by weight, preferably 2 to 20 parts by weight, and particularly preferably 3 to 15 parts by weight.

In the first embodiment of the present invention, the composition for optical materials is preferably subjected to the deaeration treatment in advance. The deaeration treatment is carried out under reduced pressure before, during or after mixing a compound which can react with a part or all of the components of the composition, a polymerization catalyst and an additive. Preferably, the deaeration treatment is carried out under reduced pressure during or after mixing. The treatment conditions are as follows: under a reduced pressure of 0.001 to 50 torr; 1 minute to 24 hours; and 0° C. to 100° C. The degree of pressure reduction is preferably 0.005 to 25 torr, and more preferably 0.01 to 10 torr. The degree of pressure reduction may be varied within these ranges. The deaeration time is preferably 5 minutes to 18 hours, and more preferably 10 minutes to 12 hours. The temperature at the time of deaeration is preferably 5 to 80° C., and more preferably 10 to 60° C. The temperature may be varied within these ranges. The operation of renewing the interface of the composition for optical materials by means of stirring, blowing a gas, vibration caused by ultrasonic wave or the like during the deaeration treatment is preferable in terms of the enhancement of the deaeration effect. Components removed by the deaeration treatment are mainly dissolved gases such as hydrogen sulfide, low-boiling substances such as low-molecular-weight thiol, etc., but the type of components to be removed is not particularly limited as long as the effects of the present invention are exerted.

In addition, the operation of filtering impurities, etc. in these composition for optical materials and/or respective raw materials before mixing by using a filter having a pore diameter of about 0.05 to 10 μm for purification is preferable in terms of further improving the quality of the optical material of the present invention.

Hereinafter, a method for producing an optical material by polymerizing the composition for optical materials of the first embodiment of the present invention will be described.

As a catalyst for polymerizing and curing the composition for optical materials of the first embodiment of the present invention, an amine, an onium salt or a phosphine compound is used. Specific examples thereof include amines, quaternary ammonium salts, quaternary phosphonium salts, tertiary sulfonium salts, secondary iodonium salts and phosphine compounds. Among them, quaternary ammonium salts, quaternary phosphonium salts and phosphine compounds, which have good compatibility with the composition, are more preferred, and quaternary phosphonium salts are even more preferred. Specifically, more preferred examples of the compounds include quaternary ammonium salts such as tetra-n-butylammonium bromide, tetraphenylammonium bromide, triethylbenzyl ammonium chloride, cetyldimethylbenzyl ammonium chloride and 1-n-dodecyl pyridinium chloride, quaternary phosphonium salts such as tetra-n-butylphosphonium bromide and tetraphenyl phosphonium bromide and phosphine compounds such as triphenyl phosphine. Among them, triethylbenzyl ammonium chloride and tetra-n-butylphosphonium bromide are even more preferred compounds, and tetra-n-butylphosphonium bromide is the most preferred compound. The polymerization catalysts may be used solely, or two or more of them may be used in combination.

The amount of the polymerization catalyst to be added cannot be determined categorically because it varies depending on the components of the composition, the mixing ratio and the method for polymerization/curing, but the amount is usually 0.001 wt % to 5 wt %, preferably 0.01 wt % to 1 wt %, and most preferably 0.01 wt % to 0.5 wt % of the total amount of the composition for optical materials. When the amount of the polymerization catalyst to be added is more than 5 wt %, the refractive index and the heat resistance of a cured product may be reduced and the product may be colored. When the amount of the polymerization catalyst to be added is less than 0.001 wt %, the composition may be insufficiently cured, resulting in insufficient heat resistance.

When polymerizing and curing the composition for optical materials, for the purpose of extension of the pot life, dispersion of heat generated by polymerization, etc., a polymerization modifier may be added according to need. Examples of the polymerization modifier include halides of groups 13 to 16 of the long form of the periodic table. Among them, halides of silicon, germanium, tin and antimony are preferred, and chlorides of germanium, tin and antimony, which have an alkyl group, are more preferred. Further, specifically, dibutyltin dichloride, butyltin trichloride, dioctyltin dichloride, octyltin trichloride, dibutyldichlorogermanium, butyltrichlorogermanium, diphenyldichlorogermanium, phenyltrichlorogermanium and triphenylantimony dichloride are even more preferred, and specifically, dibutyltin dichloride is the most preferred compound. These polymerization modifiers may be used solely, or two or more of them may be used in combination.

The amount of the polymerization modifier to be added is usually 0.0001 to 5.0 wt %, preferably 0.0005 to 3.0 wt %, and more preferably 0.001 to 2.0 wt % of the total amount of the composition for optical materials.

Further, at the time of obtaining an optical material by polymerizing and curing the composition for optical materials of the first embodiment of the present invention, it is surely possible to add publicly-known additives such as an antioxidant, an ultraviolet absorber and a blueing agent to further improve practicability of the material obtained.

Preferred examples of the antioxidant include phenol derivatives. Among them, polyhydric phenols and halogen-substituted phenols are preferred compounds, and catechol, pyrogallol and alkyl-substituted catechols are more preferred compounds, and catechol and pyrogallol are the most preferred compounds. Preferred examples of the ultraviolet absorber include benzotriazole-based compounds, and specific examples of particularly preferred compounds include 2-(2-hydroxy-5-methylphenyl)-2H-benzotriazol, 5-chloro-2-(3,5-di-tert-butyl-2-hydroxyphenyl)-2H-benzotriazol, 2-(3-tert-butyl-2-hydroxy-5-methylphenyl)-5-chloro-2H-benzotriazole, 2-(3,5-di-tert-pentyl-2-hydroxyphenyl)-2H-benzotriazole, 2-(3,5-di-tert-butyl-2-hydroxyphenyl)-2H-benzotriazole, 2-(2-hydroxy-4-octyloxyphenyl)-2H-benzotriazole and 2-(2-hydroxy-5-tert-octylphenyl)-2H-benzotriazole. Preferred examples of the blueing agent include anthraquinone-based compounds.

When the composition for optical materials of the first embodiment of the present invention is easily released from the mold during polymerization, it is possible to use or add a publicly-known external and/or internal adhesiveness improving agent to control and improve the adhesiveness between a cured product obtained and the mold. Examples of the adhesiveness improving agent include publicly-known silane coupling agents and titanate compounds, and such substances may be used solely, or two or more of them may be used in combination. The amount of the adhesiveness improving agent to be added is usually 0.0001 to 5 wt % of the total amount of the composition for optical materials. Conversely, when the composition for optical materials of the first embodiment of the present invention is not easily released from the mold after polymerization, it is possible to use or add a publicly-known external and/or internal mold release agent to improve the ability of a cured product obtained to be released from the mold. Examples of the mold release agent include fluorine-based non-ionic surfactants, silicon-based non-ionic surfactants, phosphate esters, acidic phosphate esters, oxyalkylene-type acidic phosphate esters, alkali metal salts of acidic phosphate esters, alkali metal salts of oxyalkylene-type acidic phosphate esters, metal salts of higher fatty acid, higher fatty acid esters, paraffin, wax, higher aliphatic amides, higher aliphatic alcohols, polysiloxanes and aliphatic amine ethylene oxide adducts. These substances may be used solely, or two or more of them may be used in combination. The amount of the mold release agent to be added is usually 0.0001 to 5 wt % of the total amount of the composition for optical materials.

The method for producing an optical material by polymerizing and curing the composition for optical material of the first embodiment of the present invention will be described in more detail below. All of the aforementioned respective components of the composition and additives such as antioxidant, ultraviolet absorber, polymerization catalyst, radical polymerization initiator, adhesiveness improving agent and mold release agent may be mixed together simultaneously in the same container with stirring. Alternatively, respective raw materials may be added and mixed in a stepwise fashion. Alternatively, respective several components may be separately mixed and then mixed again in the same container. Respective raw materials and auxiliary materials may be mixed in any order. The temperature to be set for mixing, the time required for mixing, etc. are basically not limited as long as respective components can be sufficiently mixed.

The composition for optical materials after the above-described reaction and treatment is injected into a mold made of glass or metal, and a polymerization and curing reaction is promoted by heating or irradiation with active energy ray such as ultraviolet light, and after that, a product obtained is released from the mold. The optical material is produced in this way. The composition for optical materials is preferably polymerized and cured by heating to produce an optical material. In this case, the curing time is 0.1 to 200 hours, usually 1 to 100 hours, and the curing temperature is −10 to 160° C., usually −10 to 140° C. The polymerization may be conducted by carrying out a step of holding the composition at a predetermined polymerization temperature for a predetermined amount of time, a step of increasing the temperature at a rate of 0.1° C. to 100° C./h and a step of decreasing the temperature at a rate of 0.1° C. to 100° C./h, or a combination of these steps. Further, in the method for producing the optical material of the present invention, it is preferred to anneal the cured product at a temperature of 50 to 150° C. for about 10 minutes to 5 hours after the completion of the polymerization in terms of eliminating distortion of the optical material. Moreover, a surface treatment such as dyeing, hard coating, impact-resistant coating, antireflection treatment and imparting antifog properties can be performed according to need.

The optical material of the present invention can be used, for example, as an optical lens.

Next, the second embodiment (preferred embodiment) of the present invention will be described.

The second embodiment of the present invention is a composition for optical materials, which comprises: a compound (a) having the structure represented by formula (1) below and having a value of turbidity in acetone of 3.0 ppm or less (episulfide compound); a polyisocyanate compound (b); and a polythiol compound (c):

(1)

wherein m represents an integer from 0 to 4, and n represents an integer of 0 or 1.

Hereinafter, raw materials to be used in the second embodiment of the present invention, i.e., the compound (a), the polyisocyanate compound (b) and the polythiol compound (c) will be described in detail.

The compound (a) to be used in the second embodiment of the present invention is a compound having the structure represented by formula (1) above. The amount of the compound (a) to be added is usually 50 to 95 wt %, preferably 55 to 90 wt %, and particularly preferably 60 to 85 wt % when the total amount of the compounds (a) to (c) is 100 wt %. When the amount of the compound (a) to be added is less than 50 wt %, the heat resistance may be reduced, and when the amount is more than 95 wt %, the strength may be reduced.

Specific examples of the compound (a) include episulfides such as bis(β-epithiopropyl)sulfide, bis(β-epithiopropyl)disulfide, bis(β-epithiopropylthio)methane, 1,2-bis(β-epithiopropylthio)ethane, 1,3-bis(β-epithiopropylthio)propane and 1,4-bis(β-epithiopropylthio)butane. As the compound (a), such compounds may be used solely, or two or more of them may be used in combination.

Among them, preferred are bis(β-epithiopropyl)sulfide (n=0 in formula (1)) and bis(β-epithiopropyl)disulfide (m=0 and n=1 in formula (1)), and most preferred is bis(β-epithiopropyl)sulfide (n=0 in formula (1)).

The amount of the polyisocyanate compound (b) to be added in the second embodiment of the present invention is usually to 25 wt %, preferably 2 to 25 wt %, and particularly preferably 5 to 20 wt % when the total amount of the compounds (a) to (c) is 100 wt %. When the amount of the compound (b) to be added is less than 1 wt %, the strength may be reduced, and when the amount is more than 25 wt %, the color tone may be reduced. As the compound (b) to be used in the second embodiment of the present invention, compounds may be used solely, or two or more of them may be used in combination.

Specific examples of the compound (b) include diethylene diisocyanate, tetramethylene diisocyanate, hexamethylene diisocyanate, trimethylhexamethylene diisocyanate, cyclohexane diisocyanate, 1,3-bis(isocyanatemethyl)cyclohexane, 1,4-bis(isocyanatemethyl)cyclohexane, isophorone diisocyanate, 2,6-bis(isocyanatemethyl)decahydronaphthalene, lysine triisocyanate, tolylene diisocyanate, o-tolidine diisocyanate, diphenylmethane diisocyanate, diphenylether diisocyanate, 342'-isocyanatecyclohexyl)propylisocyanate, isopropylidene bis(cyclohexyl isocyanate), 2,2'-bis(4-isocyanatephenyl)propane, triphenylmethane triisocyanate, bis(diisocyanatetolyl)phenylmethane, 4,4',4"-triisocyanate-2,5-dimethoxyphenylamine, 3,3'-dimethoxybenzidine-4,4'-diisocyanate, 1,3-phenyl ene diisocyanate, 1,4-phenylene diisocyanate, 4,4'-diisocyanatebiphenyl, 4,4'-diisocyanate-3,3'-dimethylbiphenyl, dicyclohexylmethane-4,4'-diisocyanate, 1,1'-methylenebis(4-isocyanatebenzene), 1,1'-methylenebis(3-methyl-4-isocyanatebenzene), m-xylylene diisocyanate, p-xylylene diisocyanate, m-tetramethyl xylylene diisocyanate, p-tetramethyl xylylene diisocyanate, 1,3-bis(2-isocyanate-2-propyl)benzene, 2,6-bis(isocyanatemethyl)naphthalene, 1,5-naphthalene diisocyanate, bis(isocyanatemethyl)tetrahydrodicyclopentadiene, bis(isocyanatemethyl)dicyclopentadiene, bis(isocyanatemethyl)tetrahydrothiophene, bis(isocyanatemethyl)norbornene, bis(isocyanatemethyl)adamantane, thiodiethyl diisocyanate, thiodipropyl diisocyanate, thiodihexyl diisocyanate, bis[(4-isocyanatemethyl)phenyl]sulfide, 2,5-diisocyanate-1,4-dithiane, 2,5-diisocyanatemethyl-1,4-dithiane, 2,5-diisocyanatemethylthiophene, dithiodiethyl diisocyanate and dithiodipropyl diisocyanate.

Preferred examples of the compound (b) include isophorone diisocyanate, tolylene diisocyanate, diphenylmethane diisocyanate, hexamethylene diisocyanate, m-xylylene diisocyanate, p-xylylene diisocyanate, m-tetramethyl xylylene diisocyanate, p-tetramethyl xylylene diisocyanate, 1,3-bis(isocyanatemethyl)cyclohexane, 1,4-bis(isocyanatemethyl)cyclohexane, bis(isocyanatemethyl)norbornene and 2,5-diisocyanatemethyl-1,4-dithiane. Particularly preferred examples of the compound (b) include isophorone diisocyanate, m-xylylene diisocyanate, 1,3-bis(isocyanatemethyl)cyclohexane, bis(isocyanatemethyl)norbornene and 2,5-diisocyanatemethyl-1,4-dithiane.

The amount of the polythiol compound (c) to be added in the second embodiment of the present invention is usually 1 to 25 wt %, preferably 2 o 25 wt %, and particularly preferably 5 to 20 wt % when the total amount of the compounds (a) to (c) is 100 wt %. When the amount of the compound (c) to be added is less than 1 wt %, the oxidation resistance may be reduced, and when the amount is more than 25 wt %, the heat resistance may be reduced. As the compound (c) to be used in the second embodiment of the present invention, compounds may be used solely, or two or more of them may be used in combination.

Specific examples of the compound (c) include methanedithiol, methanetrithiol, 1,2-dimercaptoethane, 1,2-dimercaptopropane, 1,3-dimercaptopropane, 2,2-dimercaptopropane, 1,4-dimercaptobutane, 1,6-dimercaptohexane, bis(2-mercaptoethyl)ether, bis(2-mercaptoethyl)sulfide, 1,2-bis(2-mercaptoethyloxy)ethane, 1,2-bis(2-mercaptoethylthio)ethane, 2,3-dimercapto-1-propanol, 1,3-dimercapto-2-propanol, 1,2,3-trimercaptopropane, 2-mercaptomethyl-1,3-dimercaptopropane, 2-mercaptomethyl-1,4-dimercaptobutane, 2-(2-mercaptoethylthio)-1,3-dimercaptopropane, 4-mercaptomethyl-1,8-dimercapto-3,6-dithiaoctane, 2,4-dimercaptomethyl-1,5-dimercapto-3-thiapentane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, 1,1,1-tris(mercaptomethyl)propane, tetrakis(mercaptomethyl)methane, ethyleneglycol bis(2-mercaptoacetate), ethyleneglycol bis(3-mercaptopropionate), diethyleneglycol bis(2-mercaptoacetate), diethyleneglycol bis(3-mercaptopropionate), 1,4-butanediol bis(2-mercaptoacetate), 1,4-butanediol bis(3-mercaptopropionate), trimethylolpropane tris(thioglycolate), trimethylolpropane tris(mercapto propionate), pentaerythritol tetrakis-thioglycolate, pentaerythritol tetrakis-mercaptopropionate, 1,2-dimercapto cyclohexane, 1,3-dimercapto cyclohexane, 1,4-dimercapto cyclohexane, 1,3-bis(mercaptomethyl)cyclohexane, 1,4-bis(mercaptomethyl)cyclohexane, 2,5-dimercaptomethyl-1,4-dithiane, 2,5-dimercaptomethyl-1,4-dithiane, 2,5-bis(2-mercaptoethylthiomethyl)-1,4-dithiane, 2,5-dimercaptomethyl-1-thiane, 2,5-dimercaptoethyl-1-thiane, 2,5- dimercaptomethylthiophene, 1,2-dimercaptobenzene, 1,3-dimercaptobenzene, 1,4-dimercaptobenzene, 1,3-bis (mercaptomethyl)benzene, 1,4-bis(mercaptomethyl) benzene, 2,2'-dimercaptobiphenyl, 4,4'-dimercaptobiphenyl, bis(4-mercaptophenyl)methane, 2,2-bis(4-mercaptophenyl) propane, bis(4-mercaptophenyl)ether, bis(4-mercaptophenyl)sulfide, bis(4-mercaptophenyl)sulfone, bis(4-mercaptomethylphenyl)methane, 2,2-bis(4-mercaptomethylphenyl) propane, bis(4-mercaptomethylphenyl)ether, bis(4-mercaptomethylphenyl)sulfide, 2,5-dimercapto-1,3,4-thiadiazole, 3,4-thiophenedithiol and 1,1,3,3-tetrakis (mercaptomethylthio)propane.

Among them, bis(2-mercaptoethyl)sulfide, 2,5-dimercaptomethyl-1,4-dithiane, 1,3-bis(mercaptomethyl)benzene, 1,4-bis(mercaptomethyl)benzene, 4-mercaptomethyl-1,8-dimercapto-3,6-dithiaoctane, 4,8-dimercaptomethyl-1,11-dimercapto-3,6,9-trithiaundecane, 4,7-dimercaptomethyl-1, 11-dimercapto-3,6,9-trithiaundecane, 5,7-dimercaptomethyl-1,11-dimercapto-3,6,9-trithiaundecane, 1,1,3,3-tetrakis(mercaptomethylthio)propane, pentaerythritol tetrakis-mercaptopropionate, pentaerythritol tetrakis-thioglycolate, trimethylolpropane tris(thioglycolate) and trimethylolpropane tris(mercapto propionate) are preferred, bis(2-mercaptoethyl) sulfide, 2,5-bis(2-mercaptomethyl)-1, 4-dithiane, 4-mercaptomethyl-1,8-dimercapto-3,6-dithiaoctane, 1,3-bis(mercaptomethyl)benzene, pentaerythritol tetrakis-mercaptopropionate and pentaerythritol tetrakis-thioglycolate are more preferred, and bis(2-mercaptoethyl) sulfide, 2,5-dimercaptomethyl-1,4-dithiane and 4-mercaptomethyl-1,8-dimercapto-3,6-dithiaoctane are most preferred.

Further, the ratio of the SH groups in the compound (c) to the NCO groups in the compound (b), i.e., [the number of the SH groups in the compound (c)/the number of the NCO groups in the compound (b)] (SH group/NCO group) is preferably 1.0 to 2.5, more preferably 1.25 to 2.25, and even more preferably 1.5 to 2.0. When the above-described ratio is less than 1.0, a cured product may turn yellow, and when the ratio is more than 2.5, the heat resistance may be reduced.

When obtaining an optical material by polymerizing and curing the composition for optical materials of the second embodiment of the present invention, it is preferred to add a polymerization catalyst to the compound (a), the compound (b) and the compound (c). As the polymerization catalyst, onium salts, in particular, quaternary ammonium salts, quaternary phosphonium salts, tertiary sulfonium salts and secondary iodonium salts are preferred. Among them, quaternary ammonium salts and quaternary phosphonium salts, which have good compatibility with the resin composition for optical materials, are more preferred, and quaternary phosphonium salts are even more preferred. More preferred examples of the polymerization catalyst include quaternary ammonium salts such as tetra-n-butylammonium bromide, triethylbenzyl ammonium chloride, cetyldimethylbenzyl ammonium chloride and 1-n-dodecyl pyridinium chloride and quaternary phosphonium salts such as tetra-n-butylphosphonium bromide and tetraphenyl phosphonium bromide. Among them, tetra-n-butylammonium bromide, triethylbenzyl ammonium chloride and tetra-n-butylphosphonium bromide are even more preferred polymerization catalysts, and tetra-n-butylphosphonium bromide is the most preferred polymerization catalyst.

The amount of the polymerization catalyst to be added cannot be determined categorically because it varies depending on the components of the composition, the mixing ratio and the method for polymerization and curing, but the amount is usually 0.0001 wt % to 10 wt %, preferably 0.001 wt % to 5 wt %, more preferably 0.01 wt % to 1 wt %, and most preferably 0.01 wt % to 0.5 wt % when the total amount of the compound (a), the compound (b) and the compound (c) is 100 wt %. When the amount of the polymerization catalyst to be added is more than 10 wt %, the composition may be rapidly polymerized and colored. When the amount of the polymerization catalyst to be added is less than 0.0001 wt %, the resin composition for optical materials may be insufficiently cured, resulting in poor heat resistance.

Moreover, in the production of the optical material according to the production method of the present invention, it is surely possible to add publicly-known additives such as an antioxidant, an ultraviolet absorber, a yellowing inhibitor, a blueing agent and a pigment to the compound (a), the compound (b) and the compound (c) to further improve practicability of the optical material obtained.

Preferred examples of the antioxidant include phenol derivatives. Among them, polyhydric phenols and halogen-substituted phenols are preferred compounds, and catechol, pyrogallol and alkyl-substituted catechols are more preferred compounds, and catechol is the most preferred compound.

Preferred examples of the ultraviolet absorber include benzotriazole-based compounds, and 2-(2-hydroxy-5-methylphenyl)-2H-benzotriazol, 5-chloro-2-(3,5-di-tert-butyl-2-hydroxyphenyl)-2H-benzotriazol, 2-(2-hydroxy-4-octylphenyl)-2H-benzotriazol, 2-(2-hydroxy-4-methoxyphenyl)-2H-benzotriazol, 2-(2-hydroxy-4-ethoxyphenyl)-2H-benzotriazol, 2-(2-hydroxy-4-butoxyphenyl)-2H-benzotriazol, 2-(2-hydroxy-4-octyloxyphenyl)-2H-benzotriazol and 2-(2-hydroxy-5-t-octylphenyl)-2H-benzotriazol are particularly preferred compounds.

The amount of each of the antioxidant and the ultraviolet absorber to be added is usually 0.01 to 5 wt % when the total amount of the compounds (a) to (c) is 100 wt %.

When polymerizing and curing the resin composition for optical materials of the second embodiment of the present invention, for the purpose of extension of the pot life, dispersion of heat generated by polymerization, etc., a polymerization modifier may be added to the compound (a), the compound (b) and the compound (c) according to need. Examples of the polymerization modifier include halides of groups 13 to 16 of the long form of the periodic table. Among them, halides of silicon, germanium, tin and antimony are preferred, and chlorides of germanium, tin and antimony, which have an alkyl group, are more preferred. Further, dibutyltin dichloride, butyltin trichloride, dioctyltin dichloride, octyltin trichloride, dibutyldichlorogermanium, butyltrichlorogermanium, diphenyldichlorogermanium, phenyltrichlorogermanium and triphenylantimony dichloride are even more preferred, and dibutyltin dichloride is the most preferred compound. These polymerization modifiers may be used solely, or two or more of them may be used in combination.

The amount of the polymerization modifier to be added is 0.0001 to 5.0 wt %, preferably 0.0005 to 3.0 wt %, and more preferably 0.001 to 2.0 wt % when the total amount of the compounds (a) to (c) is 100 wt %. When the amount of the polymerization modifier to be added is less than 0.0001 wt %, sufficient pot life cannot be ensured in the obtained optical material, and when the amount of the polymerization modifier to be added is more than 5.0 wt %, the resin composition for optical materials may not be sufficiently cured, and the heat resistance of the obtained optical material may be reduced.

The resin composition for optical materials thus obtained is injected into a mold or the like and polymerized to obtain an optical material.

At the time of cast-molding the resin composition for optical materials of the second embodiment of the present invention, it is preferred to filter and remove impurities using, for example, a filter having a pore diameter of about 0.1 to 5 μm in terms of improving the quality of the optical material of the present invention.

The resin composition for optical materials of the second embodiment of the present invention is usually polymerized as described below. Specifically, the curing time is usually 1 to 100 hours, and the curing temperature is usually −10° C. to 140° C. The polymerization is conducted by carrying out a step of retaining the composition at a predetermined polymerization temperature for a predetermined amount of time, a step of increasing the temperature at a rate of 0.1° C. to 100° C./h and a step of decreasing the temperature at a rate of 0.1° C. to 100° C./h, or a combination of these steps.

Further, it is preferred to anneal the obtained optical material at a temperature of 50 to 150° C. for about 10 minutes to 5 hours after curing is completed in terms of eliminating distortion of the optical material of the present invention. Moreover, the obtained optical material may be subjected to a surface treatment such as dyeing, hard coating, impact-resistant coating, antireflection treatment and imparting antifog properties according to need.

The optical material of the present invention can be used, for example, as an optical lens.

EXAMPLES

Hereinafter, the present invention (the first embodiment and the second embodiment) will be specifically described by way of examples. However, the present invention is not limited to these examples. Note that evaluation was made according to the below-described methods.

Value of turbidity in acetone: a value of turbidity in a solution measured when an episulfide compound is dissolved in acetone (a value of turbidity in acetone) was measured using a turbidimeter T-2600DA manufactured by Tokyo Denshoku Co., Ltd. Transparency: an optical material produced by polymerization of a composition for optical materials was used to prepare 10 lenses having a diameter of 70 mm and a lens power of +5D, and the lenses were observed under a fluorescent light in a dark room. The case where no white turbidity was observed in the 10 lenses was rated as "E (Excellent)". The case where white turbidity was not observed in 9 lenses was rated as "G (Good)". The case where white turbidity was not observed in 7 or 8 lenses was rated as "F (Fair)". The case where white turbidity was not observed in 6 lenses or less was rated as "P (Poor)". F or higher levels are regarded as acceptable.

Compound (a) (episulfide compound): bis(β-epithiopropyl) sulfides having a value of turbidity in acetone of 0.49 ppm, 1.1 ppm, 2.7 ppm or 5.1 ppm were selected and used.

Example 1A

The composition for optical materials and the optical material of the present invention were prepared according to the below-described production method A, using bis(β-epithiopropyl)sulfide having a value of turbidity in acetone of 0.49 ppm. The result regarding transparency of the obtained optical material was good (E). The results are shown in Table 1.

Examples 2A to 6A

The composition for optical materials and the optical material of the present invention were prepared according to the production method shown in Table 1, using bis(β-epithiopropyl)sulfide having a value of turbidity in acetone shown in Table 1. The results are shown in Table 1.

Comparative Examples 1A to 2A

A composition for optical materials and an optical material were prepared according to the production method shown in Table 1, using bis(β-epithiopropyl)sulfide having a value of turbidity in acetone shown in Table 1. The results are shown in Table 1.

Note that the details of the production methods for compositions for optical materials and optical materials used in the above-described Examples and Comparative Examples are as follows:

Production Method A:

To 78 parts by weight of bis(β-epithiopropyl)sulfide and 14 parts by weight of sulfur, 0.5 parts by weight of mercaptomethylimidazole was added, and the mixture was preliminarily polymerized at 60° C. The consumption rate of sulfur at that time was 50% according to HPLC analysis (GPC mode). After that, the mixture was cooled to 20° C., and then a mixed solution of 7 parts by weight of bis(2-mercaptoethyl)sulfide, 0.2 parts by weight of dibutyltin dichloride and 0.03 parts by weight of tetramethylphosphonium bromide was added thereto, and the mixture was homogeneously mixed and then deaerated, thereby preparing a composition for optical materials. Then the composition for optical materials was injected into a mold, and it was heated from 20° C. to 100° C. over 20 hours to be polymerized and cured. After that, the obtained product was released from the mold and then annealed, thereby obtaining an optical material.

Production Method B:

To 78 parts by weight of bis(β-epithiopropyl)sulfide and 14 parts by weight of sulfur, 0.5 parts by weight of mercaptomethylimidazole was added, and the mixture was preliminarily polymerized at 60° C. The consumption rate of sulfur at that time was 46% according to HPLC analysis (GPC mode). After that, the mixture was cooled to 20° C., and then a mixed solution of 7 parts by weight of 1,3-bis (mercaptomethyl)benzene, 0.2 parts by weight of dibutyltin dichloride and 0.03 parts by weight of tetramethylphosphonium bromide was added thereto, and the mixture was homogeneously mixed and then deaerated, thereby preparing a composition for optical materials. Then the composition for optical materials was injected into a mold, and it was heated from 20° C. to 100° C. over 20 hours to be polymerized and cured. After that, the obtained product was released from the mold and then annealed, thereby obtaining an optical material.

TABLE 1

|  | Episulfide compound | Value of turbidity in acetone | Production method | Transparency |
| --- | --- | --- | --- | --- |
| Example 1A | Bis(β-epithiopropyl)sulfide | 0.49 ppm | A | E |
| Example 2A | Bis(β-epithiopropyl)sulfide | 0.49 ppm | B | E |
| Example 3A | Bis(β-epithiopropyl)sulfide | 1.1 ppm | A | G |
| Example 4A | Bis(β-epithiopropyl)sulfide | 1.1 ppm | B | G |
| Example 5A | Bis(β-epithiopropyl)sulfide | 2.7 ppm | A | F |
| Example 6A | Bis(β-epithiopropyl)sulfide | 2.7 ppm | B | F |

TABLE 1-continued

| Episulfide compound | | Value of turbidity in acetone | Production method | Transparency |
|---|---|---|---|---|
| Comparative Example 1A | Bis(β-epithiopropyl)sulfide | 5.1 ppm | A | P |
| Comparative Example 2A | Bis(β-epithiopropyl)sulfide | 5.1 ppm | B | P |

Example 1B

To (a) 1320 g of bis(β-epithiopropyl)sulfide having a value of turbidity in acetone of 0.49 ppm, (b) 340 g of isophorone diisocyanate and (c) 340 g of bis(2-mercaptoethyl)sulfide, 20 g of 2-(2-hydroxy-5-t-octylphenyl)-2H-benzotriazole as an ultraviolet absorber, 0.2 g of Zelec UN (manufactured by Stepan) as a mold release agent and 2 g of tetra-n-butylphosphonium bromide as a polymerization catalyst were added, and the mixture was well mixed homogeneously at 20° C. After that, the obtained mixture was subjected to the deaeration treatment at a vacuum degree of 4 kPa, and the resin composition for optical materials was injected into a mold for a semifinished lens having a mold diameter of 75 mm, a central thickness of 7 mm and an edge thickness of 15 mm, which was composed of two glass plates and a tape, and it was heated at 30° C. for 30 hours, then the temperature was elevated to 100° C. over 10 hours at a constant rate, and finally, it was heated at 100° C. for 1 hour to be polymerized and cured. After cooling, the obtained product was released from the mold and annealed at 110° C. for 60 minutes, and after that, transparency was visually observed. The evaluation of transparency of the obtained optical material is shown in Table 2. The ratio of the SH groups in the compound (c) to the NCO groups in the compound (b), i.e., [the number of the SH groups in the compound (c)/the number of the NCO groups in the compound (b)] (SH group/NCO group) was 1.4.

Examples 2B to 6B

The process was carried out in a manner similar to that in Example 1B, except that the compound (a) used and the value of turbidity in acetone thereof are as shown in Table 2. The evaluation of transparency of the obtained optical material is shown in Table 2.

Comparative Examples 1B to 2B

The process was carried out in a manner similar to that in Example 1B, except that the compound (a) used and the value of turbidity in acetone thereof are as shown in Table 2. The evaluation of transparency of the obtained optical material is shown in Table 2.

TABLE 2

| Examples | Compound (a) | Value of turbidity in acetone | Transparency |
|---|---|---|---|
| Example 1B | Bis(β-epithiopropyl)sulfide | 0.49 ppm | E |
| Example 2B | Bis(β-epithiopropyl)disulfide | 0.49 ppm | E |
| Example 3B | Bis(β-epithiopropyl)sulfide | 1.1 ppm | G |
| Example 4B | Bis(β-epithiopropyl)disulfide | 1.1 ppm | G |
| Example 5B | Bis(β-epithiopropyl)sulfide | 2.7 ppm | F |
| Example 6B | Bis(β-epithiopropyl)disulfide | 2.7 ppm | F |
| Comparative Example 1B | Bis(β-epithiopropyl)sulfide | 5.1 ppm | P |
| Comparative Example 2B | Bis(β-epithiopropyl)disulfide | 5.1 ppm | P |

In the above-described Examples, by polymerizing the composition for optical materials containing the episulfide compound which satisfies the condition that the value of turbidity in acetone is 3.0 ppm or less, white turbidity after curing was successfully prevented and good transparency was successfully realized. Therefore, according to the present invention, it is possible to predict the possibility of occurrence of white turbidity after polymerization and curing and judge whether it is good or bad prior to polymerization and curing, and to produce only optical materials having good properties in a selective manner. Therefore, it is possible to realize both effective use of the composition for optical materials and production of excellent optical materials.

The invention claimed is:

1. A composition for optical materials, which comprises an episulfide compound having a value of turbidity in acetone of 3.0 ppm or less.

2. The composition for optical materials according to claim 1, further comprising sulfur.

3. The composition for optical materials according to claim 2, wherein the episulfide compound is first polymerized with sulfur followed by a further polymerization.

4. The composition for optical materials according to claim 2, wherein 10% or more of the sulfur is first polymerized with the episulfide compound followed by a further polymerization.

5. The composition for optical materials according to claim 2, further comprising a polythiol compound.

6. The composition for optical materials according to claim 1, which has been subjected to deaeration treatment.

7. The composition for optical materials according to claim 1, wherein the episulfide compound is a compound (a) having the structure represented by formula (1) below:

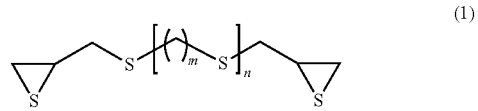

wherein m represents an integer from 0 to 4, and n represents an integer of 0 or 1.

8. The composition for optical materials according to claim 7, further comprising a polyisocyanate compound (b) and a polythiol compound (c).

9. The composition for optical materials according to claim 8, wherein the compound (b) is at least one compound selected from the group consisting of isophorone diisocyanate, tolylene diisocyanate, diphenylmethane diisocyanate, hexamethylene diisocyanate, m-xylylene diisocyanate, p-xylylene diisocyanate, m-tetramethyl xylylene diisocyanate, p-tetramethyl xylylene diisocyanate, 1,3-bis(isocyanatemethyl)cyclohexane, 1,4-bis(isocyanatemethyl)cyclohexane, bis(isocyanatemethyl)norbornene and 2,5-diisocyanatemethyl-1,4-dithiane, and the compound (c) is at least one compound selected from the group consisting of bis(2-mercaptoethyl)sulfide, 2,5-dimercaptomethyl-1,4-dithiane, 1,3-bis(mercaptomethyl)benzene, 1,4-bis(mercaptomethyl)benzene, 4-mercaptomethyl-1,8-dimercapto-3,6-dithiaoctane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, 1,1,3,3-tetrakis(mercaptomethylthio)propane, pentaerythritol tetrakis-mercaptopropionate, pentaerythritol tetrakis-thioglycolate, trimethylolpropane tris(thioglycolate) and trimethylolpropane tris(mercapto propionate).

10. The composition for optical materials according to claim 8, wherein, when the total amount of the compound (a), the compound (b) and the compound (c) is 100 wt %, the compound (a) is in an amount of 50 to 95 wt %; the compound (b) is in an amount of 1 to 25 wt %; and the compound (c) is in an amount of 1 to 25 wt %, and wherein the ratio of the number of SH groups in the compound (c) to the number of NCO groups in the compound (b) is 1.0:1.0 to 2.5:1.0.

11. A method for producing an optical material, which comprises polymerizing and curing the composition for optical materials according to claim 1.

12. A method for producing an optical material, which comprises adding an onium salt, as a polymerization catalyst, to the composition for optical materials according to claim 8 in an amount of 0.0001 to 10 wt % relative to the total amount of the compounds (a) to (c) and polymerizing and curing the mixture.

13. The method for producing an optical material according to claim 11, which comprises polymerizing and curing the composition for optical materials and then annealing it.

14. An optical material obtained by the method for producing an optical material according to claim 11.

15. An optical lens comprising the optical material according to claim 14.

16. The composition for optical materials according to claim 2, wherein the episulfide compound is polymerized with sulfur before a polymerizing reaction that produces the optical material.

17. The composition for optical materials according to claim 2, wherein 10% or more of the sulfur is polymerized with the episulfide compound before a polymerizing reaction that produces the optical material.

18. A method for producing a raw material for optical materials from a product of an episulfide compound, comprising polymerizing a product of an episulfide compound having a value of turbidity in acetone of 3.0 ppm or less into the raw material for optical materials.

19. The method for producing a raw material for optical materials according to claim 18, wherein the episulfide compound is a compound (a) having the structure represented by formula (1) below:

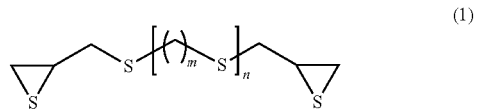

wherein m represents an integer from 0 to 4, and n represents an integer of 0 or 1.

* * * * *